United States Patent
Ding et al.

(10) Patent No.: US 7,060,865 B2
(45) Date of Patent: Jun. 13, 2006

(54) RECOVERY OF C4 OLEFINS FROM A PRODUCT STREAM COMPRISING C4 OLEFINS, DIMETHYL ETHER AND C5+ HYDROCARBONS

(75) Inventors: Zhong Yi Ding, Houston, TX (US); James Richardson Lattner, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 647 days.

(21) Appl. No.: 10/292,232

(22) Filed: Nov. 12, 2002

(65) Prior Publication Data

US 2004/0092778 A1   May 13, 2004

(51) Int. Cl.
*C07C 7/04*      (2006.01)
*C07C 7/11*      (2006.01)
*C07C 41/42*   (2006.01)
*C07C 41/38*   (2006.01)

(52) U.S. Cl. ............... 585/800; 203/14; 203/49; 203/94; 203/98; 208/100; 208/101; 208/185; 208/187; 208/347; 208/356; 208/362; 568/697; 568/699; 585/18; 585/264; 585/502; 585/510; 585/518; 585/639; 585/640; 585/809

(58) Field of Classification Search ............... 203/14, 203/49, 94, 98; 208/100, 101, 185, 187, 208/347, 356, 362; 568/697, 699; 585/18, 585/264, 502, 510, 518, 800, 639, 640, 809
See application file for complete search history.

(56) References Cited

U.S. PATENT DOCUMENTS

| | | | |
|---|---|---|---|
| 4,474,647 A | 10/1984 | Asselineau et al. | 203/49 |
| 4,603,225 A * | 7/1986 | Colaianne et al. | 568/697 |
| 5,112,236 A | 5/1992 | Martin et al. | 439/86 |
| 5,122,236 A * | 6/1992 | Smith et al. | 203/43 |
| 5,336,841 A | 8/1994 | Adams | 585/834 |
| 5,609,734 A | 3/1997 | Streicher et al. | 203/39 |
| 5,714,662 A | 2/1998 | Vora et al. | 585/640 |
| 6,100,438 A * | 8/2000 | Marion et al. | 585/639 |
| 2004/0039239 A1* | 2/2004 | Shutt | 585/639 |

FOREIGN PATENT DOCUMENTS

| | | |
|---|---|---|
| EP | 0 065 112 | 11/1982 |
| EP | 0 229 994 | 7/1987 |

* cited by examiner

*Primary Examiner*—Walter D. Griffin
*Assistant Examiner*—Prem C. Singh

(57) ABSTRACT

Disclosed is a process for removing DME from a stream containing C4 olefins. The process includes providing a first stream comprising C4 olefins, C5+ hydrocarbons, DME, and methanol. The first stream is separated into a second stream comprising the C4 olefins and the DME and a third stream comprising the C5+ hydrocarbons and the methanol. The second stream is directed to a DME absorption unit, wherein the second stream contacts water under conditions effective to separate the C4 olefins from the DME. Also disclosed is a process including contacting the first stream with water in a methanol removal unit under conditions effective to separate remove the methanol therefrom; distilling the methanol-depleted stream to remove C5+ hydrocarbon components, and contacting the stream with water in a DME removal unit under conditions effective to form an overhead stream comprising the C4 olefins and a bottoms stream comprising the DME.

40 Claims, 4 Drawing Sheets

RECOVERY OF C4 OLEFINS FROM A PRODUCT STREAM COMPRISING C4 OLEFINS, DIMETHYL ETHER AND C5+ HYDROCARBONS

FIELD OF THE INVENTION

The present invention relates to C4 olefin recovery systems. More particularly, the present invention relates to recovering C4 olefins from a mixed olefin feedstock comprising C4 olefins, C5+ hydrocarbons and dimethyl ether.

BACKGROUND OF THE INVENTION

The petrochemical industry has known for some time that oxygenates, especially alcohols, are convertible into light olefin(s) such as ethylene and propylene. Ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide. The preferred conversion process is generally referred to as a methanol-to-olefin(s) (MTO) process, where methanol is converted to primarily ethylene and/or propylene in the presence of a molecular sieve catalyst.

Butenes (C4 olefins) are formed as beneficial byproducts of the MTO process. Butenes may be used to produce a variety of commercially important products including fuels, polymers, plasticizers, and other chemical products. For example, a butenes feedstock may be used to make alkylate fuels, a gasoline additive known as methyl-t-butyl ether (MTBE), and linear low-density polyethylene. 2-butenes are the most desirable isomers for the production of alkylates. Isobutene is used primarily to make MTBE, and 1-butene is used as a co-monomer for making linear low-density polyethylene or as a monomer in polybutene production. The worldwide market for butenes is approaching 1 billion pounds per year.

U.S. Pat. No. 5,714,662 to Vora et al. provides a practical use for a $C_3$ and $C_4$ olefin stream separated from an MTO product effluent. More specifically, the Vora et al. patent is directed to a process for producing light olefins from crude methanol. The patent discloses that propylene and butylene fractions from the MTO product effluent can be converted to high octane ether and other high value products. Optionally, butenes from the MTO process can be dimerized and hydrogenated to produce a $C_8$ alkylate having a high octane for use in blending motor gasoline.

Generally undesirable byproducts, such as $C_5$+ hydrocarbons (olefins and non-olefins), and oxygenate compounds such as alcohols, aldehydes, ketones, esters, acids and ethers in the $C_1$ to $C_6$ range as well as trace quantities of aromatic compounds can also be formed in MTO reactors or in MTO effluent processing. Additionally, a small amount of oxygenate from the feedstock, e.g., methanol or dimethyl ether ("DME"), can pass through the MTO reactor with the product effluent without being converted to desired product. As a result of oxygenate synthesis and/or oxygenate "pass through" in an MTO reactor system, the effluent from an MTO reactor can contain undesirably high concentrations of oxygenate compounds.

Due to the commercial value of C4 olefins, various processing schemes have been developed for separating C4 olefins from oxygenate and heavy hydrocarbon contaminants in both MTO and non-MTO effluent streams. For example, U.S. Pat. No. 5,336,841 to Adams is directed to a process for removing oxygenates from a C4 raffinate stream from an MTBE plant. A back-cracking catalyst is placed into the bottom of an oxygenate removal column, which converts any MTBE or tertiary butyl alcohol contained therein back to their original components of isobutene and methanol or water. The raffinate stream is first subjected to a water wash to remove the gross amounts of methanol and DME.

U.S. Pat. No. 5,122,236 to Smith et al. is directed to a process for removing DME and methanol impurities from a C4 hydrocarbon stream without substantial loss of C4 hydrocarbons by fractionating a C4 hydrocarbon stream containing DME and methanol at low levels, e.g., less than 5 weight percent, to produce an overhead of about 20 to 40 volume percent of the C4 stream, condensing the overhead, contacting the condensed overhead with about 1 to 5 volumes of water, thereby removing a portion of the DME and methanol from the C4 stream, returning substantially all of the C4 stream, except the small amount solubilized in the water, to the fractionation and flashing the solubilized DME and hydrocarbons from the water.

Separation of DME from C4 olefins has proven inefficient when the feed stream contains a mixture of DME, C4 olefins, C5+ hydrocarbons and coboiling oxygenates. Thus, a need exists for efficiently separating these generally undesirable heavy hydrocarbons and oxygenates from the desirable C4 olefins in an MTO effluent stream, or from a similar effluent stream derived from another reaction process.

SUMMARY OF THE INVENTION

It has been discovered that by first separating out C5+ hydrocarbons and coboiling oxygenates, if any, from a stream comprising C5+ hydrocarbons, DME and C4 hydrocarbons, a more efficient separation of DME from C4 olefins by water wash is obtainable.

The present invention provides a process for removing DME from a stream containing C4 olefins and C5+ hydrocarbons. The process includes providing a first stream comprising C4 olefins, C5+ hydrocarbons, DME, and, optionally, methanol. The first stream is separated into a second stream comprising the C4 olefins and the DME and a third stream comprising the C5+ hydrocarbons and the methanol. The second stream is directed to a DME absorption unit, wherein the second stream contacts water under conditions effective to separate the C4 olefins from the DME. Optionally, the third stream is directed to a methanol absorption unit, wherein the third stream contacts water under conditions effective to separate the C5+ hydrocarbons from the methanol.

One embodiment of the present invention includes a process for removing DME from a stream containing C4 olefins. The process includes providing an initial stream comprising C4 olefins, C5+ hydrocarbons, DME, and methanol. The initial stream contacts water in a methanol removal unit under conditions effective to separate the stream into a first overhead stream comprising the C4 olefins, the DME and the C5+ hydrocarbons, and a first bottoms stream comprising the methanol. The first overhead stream is separated into a second overhead stream comprising the C4 olefins and the DME, and a second bottoms stream comprising the C5+ hydrocarbons. The second overhead stream contacts water in a DME removal unit under conditions effective to separate the second overhead stream into a third overhead stream comprising the C4 olefins and a third bottoms stream comprising the DME.

Another embodiment is directed to a process for removing DME from a stream containing C4 olefins. The process includes providing a product stream from an methanol-to-olefin reaction system, the product stream comprising greater than 30 combined molar percent of DME and C4 olefins. The stream contacts water in a DME removal unit under conditions effective to separate the C4 olefins from the DME. As used herein, "molar percent" is based on the total moles of all components in a specified stream.

In another embodiment, the invention is directed to a process for removing DME from a stream containing C4 olefins, the process including providing a product stream from a methanol-to-olefin reaction system, the product stream comprising DME, butenes, C5+ hydrocarbons and coboiling oxygenates. The C5+ hydrocarbons and the coboiling oxygenates are removed from the product stream to form a processed stream comprising the DME and the butenes. The processed stream contacts water in a DME removal unit under conditions effected to separate the DME from the butenes.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Figure 1:
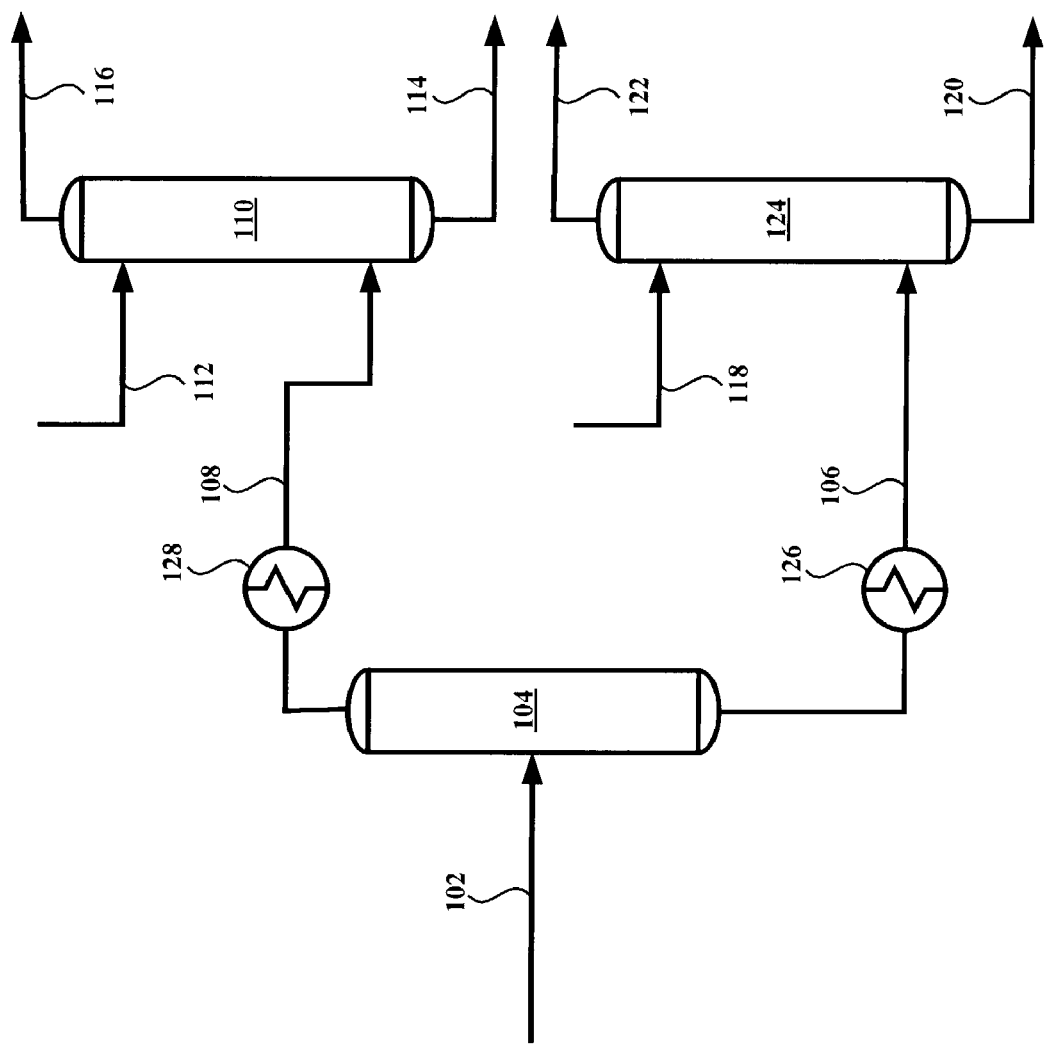
FIG. 1 illustrates one embodiment of a separation scheme.

The present invention provides a new highly efficient separation process and system for separating dimethyl ether (DME) from C4 olefins present in an effluent stream comprising DME, C4 olefins, C5+ hydrocarbons and, optionally, methanol. The inventors have discovered that the best separation of DME and C4 olefins by water wash is obtained when the major components in the stream are DME and C4 olefins; it is particularly desirable to first separate methanol, other oxygenates, and C5+ hydrocarbons from the DME and the C4 olefins, followed by separating the DME from the C4 olefins by washing with a DME removal medium such as water.

In a first embodiment of the present invention, a first stream (initial effluent stream) comprising C4 olefins, C5+ hydrocarbons, DME and, optionally, methanol (and/or one or more other oxygenates that coboil with C5+ hydrocarbons) is subjected to distillation in a distillation column designed to form an overhead stream comprising the C4 olefins and DME. The bottoms stream from the distillation column comprises the methanol, if any, other coboiling oxygenates, if any, and the C5+ hydrocarbons. As used herein, "coboiling oxygenates" means one or more oxygenate compounds having a boiling point between about 0° F. (−17° C.) to about 302° F. (150° C.). More preferably, the coboiling oxygenates have a boiling point between about 32° F. (150° C.) and about 266° F. (130° C.), and most preferably between about 68° F. (20° C.) and about 225° F. (107° C.). A DME absorption medium, e.g., water, then contacts the overhead stream in a wash column under conditions effective to efficiently separate the DME from the C4 olefins.

In a second embodiment of the present invention, a first stream (initial effluent stream) comprising C4 olefins, C5+ hydrocarbons, DME and, optionally, methanol (and/or one or more other oxygenates that coboil with C5+ hydrocarbons) contacts a coboiling oxygenate absorption medium, e.g., water, in a wash column under conditions effective to separate the methanol, if any, and other coboiling oxygenates, if any, from the first stream. The wash column overhead stream comprising DME, C4 olefins and C5+ hydrocarbons is then directed to a distillation column wherein the wash column overhead stream is distilled under conditions effective to form a second overhead stream comprising DME and C4 olefins, and a second bottoms stream comprising the C5+ hydrocarbons. The second overhead stream is then directed to a second wash column wherein the second overhead stream contacts a DME removal medium, e.g., water, under conditions effective to efficiently separate the DME from the C4 olefins.

The initial effluent stream may be derived from a variety of sources. For example, in one embodiment, the initial stream is derived from a product effluent of a reaction selected from the group consisting of an olefin interconversion reaction, an oxygenate to gasoline conversion reaction, malaeic anhydride formulation, vapor phase methanol synthesis, phthalic anhydride formulation, a Fischer Tropsch reaction, and an acrylonitrile formulation. Preferably, the initial effluent stream is an effluent stream from a methanol to olefin (MTO) reaction system.

Preferably, the initial effluent stream that is to be processed according to the present invention is rich in C4 olefins. The initial effluent stream preferably comprises at least 10 molar percent C4 olefins, more preferably at least 20 or 30 molar percent C4 olefins, and most preferably more than 40 or 50 molar percent C4 olefins. In terms of ranges, the initial effluent stream optionally comprises from 10 to 90 molar percent C4 olefins, 20 to 60 molar percent C4 olefins, or 40 to 60 molar percent C4 olefins. The initial effluent stream optionally includes other hydrocarbons such as C3-hydrocarbons, or C5+ hydrocarbons such as pentene, pentane, hexene, hexane, heptane, etc. As used herein, "molar percent" is based on the total moles of all components in a specified stream.

If the initial effluent stream includes C3-hydrocarbons, the initial effluent stream preferably comprises less than 20 molar percent C3-hydrocarbons, more preferably less than 10 molar percent C3-hydrocarbons, more preferably less than 5 molar percent C3-hydrocarbons, and most preferably less than 2 molar percent C3-hydrocarbons. In terms of lower range limits, the initial effluent stream optionally comprises more than 1, more than 2 or more than 3 molar percent C3-hydrocarbons.

The initial effluent stream also optionally includes butane. If the effluent stream includes butane, the effluent stream preferably comprises less than 15 molar percent butane, more preferably less than 10 molar percent butane, and most preferably less than 5 molar percent butane. In terms of lower range limits, the effluent stream optionally comprises more than 0.5, more than 1, or more than 2 molar percent butane.

If the initial effluent stream comprises C5+ hydrocarbons, the initial effluent stream preferably comprises less than 40 molar percent C5+ hydrocarbons, more preferably less than 25 molar percent C5+ hydrocarbons, more preferably less than 15 molar percent C5+ hydrocarbons, and most preferably less than 10 molar percent C5+ hydrocarbons. In terms of lower range limits, the initial effluent stream optionally comprises more than 5, more than 10 or more than 15 molar percent C5+ hydrocarbons.

The initial effluent stream also optionally includes water. More specifically, the initial effluent stream optionally comprises less than 15 molar percent water, more preferably less than 10 molar percent water and most preferably less than 5 molar percent water. In terms of lower range limits, the initial effluent stream optionally comprises more than 0.1, more than 2 or more than 10 molar percent water.

The initial effluent stream also optionally comprises oxygenates such as methanol, DME, and/or C1–C5 aldehydes, alcohols, ketones or acids. If the initial effluent stream includes methanol, the initial effluent stream preferably comprises less than 45 molar percent methanol, more preferably less than 35 molar percent methanol, more preferably less than 20 molar percent methanol, and most preferably less than 2 molar percent methanol. In terms of lower range limits, the initial effluent stream optionally comprises more than 0.5, more than 5 or more than 30 molar percent methanol. If the initial effluent stream includes DME, the initial effluent stream preferably comprises less than 20 molar percent DME, more preferably less than 10 molar percent DME, and most preferably less than 5 molar percent DME. In terms of lower range limits, the initial effluent stream optionally comprises more than 0.5, more than 2, more than 5 or more than 10 molar percent DME. Preferably, the initial effluent stream includes greater than 30, more preferably greater than 40, and most preferably greater than 60, combined molar percent of DME and C4 olefins. If the initial effluent stream comprises other oxygenates, the initial effluent stream preferably comprises less than 20 molar percent other oxygenates, more preferably less than 10 molar percent other oxygenates, and most preferably less than 5 molar percent other oxygenates. In terms of lower range limits, the initial effluent stream optionally comprises more than 0.5, more than 2, more than 5 or more than 10 molar percent other oxygenates.

The preferred initial effluent stream can also be expressed in terms of butylene component ratios. For example, the ratio of 1-butene to the sum of isobutene, butadiene and 2-butene preferably is greater than 0.10, more preferably greater than 0.20, and most preferably greater than 0.25.

FIG. 1 illustrates one embodiment of the present invention wherein distillation of an initial effluent stream to separate DME and C4 olefins from C5+ hydrocarbons, and optionally from coboiling oxygenates such as methanol, is followed by contacting an overhead stream from the distillation unit with a DME removal medium under conditions effective to separate the DME from the C4 olefins. Initial effluent stream 102, comprising C5+ hydrocarbons, C4 olefins, and DME, is shown entering distillation column 104. Optionally, initial effluent stream 102 further comprises methanol or other oxygenates that coboil with C5+ hydrocarbons. In the distillation column the initial effluent stream is subjected to conditions effective to separate more volatile components from less volatile components contained therein. A first overhead stream 108 comprising more volatile components exits an upper section of the distillation column 104 and less volatile components exit the distillation column 104 through first bottoms stream 106. Specifically, distillation column 104 should be designed such that first overhead stream 108 comprises at least a majority of the C4 olefins and DME that was contained in initial effluent stream 102. More desirably, first overhead stream 108 comprises more than 50 molar percent, more preferably more than 75 molar percent and most preferably more than 95 molar percent of the C4 olefins contained in initial effluent stream 102. Similarly, first overhead stream 108 preferably comprises more than 50 molar percent, more preferably more than 75 molar percent and most preferably more than 95 molar percent of the DME contained in initial effluent stream 102. Distillation column 104 should also be designed such that first bottoms stream 106 comprises at least a majority of the C5+ hydrocarbons that was contained in initial effluent stream 102. More desirably, first bottoms stream 106 comprises more than 50 molar percent, more preferably more than 75 molar percent and most preferably more than 95 molar percent of the C5+ hydrocarbons that was contained in initial effluent stream 102. If the initial effluent stream 102 comprises oxygenate compounds that co-boil with C5+ hydrocarbons, the first bottoms stream 106 preferably comprises at least a majority of the coboiling oxygenates that was contained in initial effluent stream 102. First bottoms stream 106 preferably comprises more than 75 molar percent, more preferably more than 90 molar percent and most preferably more than 95 molar percent of the coboiling oxygenates contained in initial effluent stream 102. A non-limiting exemplary list of oxygenates that coboil with C5+ hydrocarbons includes methanol, ethanol, acetaldehyde, acetone, propanol, propanal, butanol, butanone, butanal, pentanol, pentanone, and pentanal. By first separating C5+ hydrocarbons and coboiling oxygenates, if any, from an initial effluent stream comprising C5+ hydrocarbons, C4 olefins and DME, an efficient separation of the C4 olefins and DME is subsequently obtainable.

With continuing reference to FIG. 1, after optionally passing through a heat exchanger 128 that is adapted to cool first overhead stream 108, the first overhead stream is directed to a first wash unit 110. In the wash unit, a DME removal medium, such as water, contacts the first overhead stream 108 under conditions effective to separate the DME from the C4 olefins. The DME removal medium is shown entering the first wash unit 110 via line 112. Specifically, C4 olefins exit through the top of first wash unit 110 via second overhead stream 116. Preferably, second overhead stream 116 comprises a majority of the C4 olefins that were present in the first overhead stream 108. More preferably, second overhead stream 116 comprises more than 90 molar percent, more preferably more than 95 molar percent, and most preferably more than 99 molar percent of the C4 olefins that were present in the first overhead stream 108. A minor amount of DME may be present in the second overhead stream 116. The DME content in the second overhead stream 116 will depend upon the DME removal medium treating rate, the number of stages and the temperature of the extraction column, and optionally is adjusted to meet the C4 quality requirements as needed. The DME and the DME removal medium exit the wash unit 110 via second bottoms stream 114. Preferably, second bottoms stream 114 comprises a majority of the DME that was present in the first overhead stream 108. More preferably, second bottoms stream 114 comprises more than 50 molar percent, more preferably more than 90 molar percent, and most preferably more than 98 molar percent of the DME that was present in the first overhead stream 108. The DME is easily recoverable from the second bottoms stream 114, for example, by distillation, and then optionally recycled to the MTO reactor.

After optionally passing through a heat exchanger 126 that is adapted to cool first bottoms stream 106, the first bottoms stream from distillation column 104 optionally is treated to separate the C5+ hydrocarbons from coboiling oxygenates. With continuing reference to FIG. 1, first bottoms stream 106 is directed to a second wash unit 124. In the second wash unit, an oxygenate removal medium, such as water, contacts the first bottoms stream 106 under conditions effective to separate coboiling oxygenates, such as methanol, from the C5+ hydrocarbons. The oxygenate removal medium is shown entering the second wash unit 124 via line 118. Specifically, C5+ hydrocarbons exit through the top of second wash unit 124 via third overhead stream 122. Preferably, third overhead stream 122 comprises a majority of the C5+ hydrocarbons that were present in the first bottoms stream 106. More preferably, third overhead stream 122 comprises more than 50 molar percent, more preferably more than 75 molar percent, and most preferably more than 95 molar percent of the C5+ hydrocarbons that were present in the first bottoms stream 106. The one or more oxygenates and the oxygenate removal medium exit the second wash unit 124 via third bottoms stream 120. Preferably, third bottoms stream 120 comprises a majority of the oxygenates that was present in the first bottoms stream 106. More preferably, third bottoms stream 120 comprises more than 75 molar percent, more preferably more than 90 molar percent, and most preferably more than 95 molar percent of the oxygenates that were present in the first bottoms stream 106.

Figure 2:
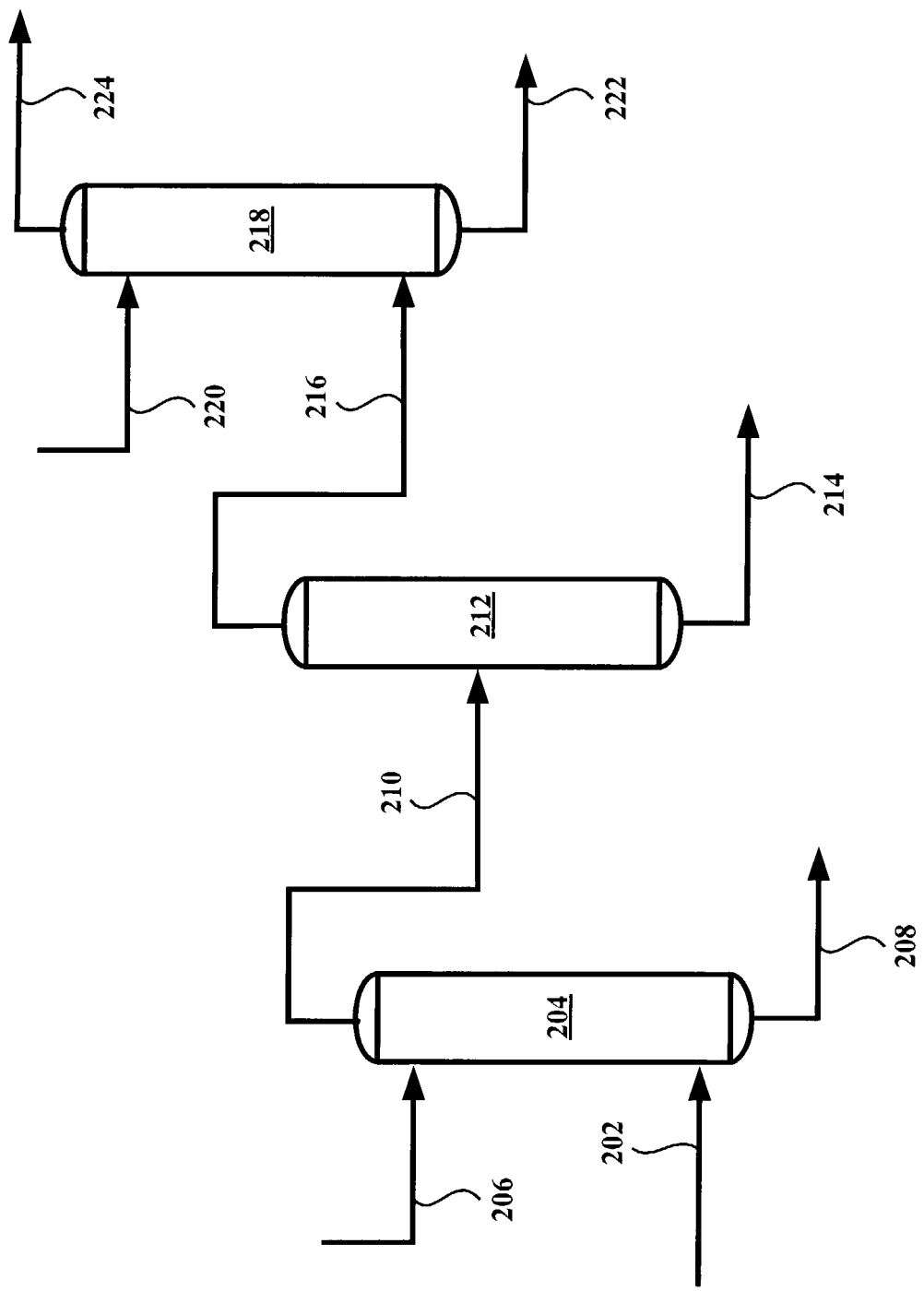
FIG. 2 illustrates another embodiment of a separation scheme.

FIG. 2 illustrates another embodiment of the present invention wherein an initial effluent stream 202 comprising C4 olefins, DME, C5+ hydrocarbons and, optionally, one or more oxygenates that coboil with C5+ hydrocarbons is subjected to a separation scheme having two wash steps and an distillation step between the wash steps. As shown in FIG. 2, an initial effluent stream 202 comprising C4 olefins, DME, C5+ hydrocarbons and, optionally, one or more oxygenates that coboil with C5+ hydrocarbons is directed to an oxygenate removal unit, preferably first wash unit 204. In the first wash unit, the initial effluent stream contacts an oxygenate removal medium under conditions effective to remove the coboiling oxygenates, if any, from the initial effluent stream 202. Oxygenate removal medium, e.g., water, is shown entering first wash unit 204 via line 206. The oxygenate removal medium contacts the coboiling oxygenates, if any, and exits the first wash unit 204 through first bottoms stream 208. First bottoms stream 208 preferably comprises a majority of the oxygenates that coboil with C5+ hydrocarbons that were present in the initial effluent stream 202. Preferably, first bottoms stream 208 comprises more than 50 molar percent, more preferably more than 75 molar percent, and most preferably more than 95 molar percent of the oxygenates that coboil with C5+ hydrocarbons that were present in the initial effluent stream 202. The majority of the C4 olefins, C5+ hydrocarbons, and DME exits first wash unit 204 through first overhead stream 210. Preferably, first overhead stream 210 comprises more than 50 molar percent, more preferably more than 75 molar percent, and most preferably more than 95 molar percent of the C5+ hydrocarbons that were present in the initial effluent stream 202. First overhead stream 210 also preferably comprises more than 10 molar percent, more preferably more than 50 molar percent, and most preferably more than 90 molar percent of the DME that was present in the initial effluent stream 202. First overhead stream 210 also preferably comprises more than 75 molar percent, more preferably more than 90 molar percent, and most preferably more than 95 molar percent of the C4 olefins that were present in the initial effluent stream 202.

First overhead stream 210 is then directed to a C5+ hydrocarbon removal unit, which preferably is a distillation column 212. In distillation column 212, C5+ hydrocarbons are removed from the first overhead stream 210. Specifically, first overhead stream 210 is heated under conditions effective to form a second overhead stream 216 comprising DME and C4 olefins, and a second bottoms stream 214 comprising C5+ hydrocarbons. The majority of the C4 olefins and DME exits distillation column 212 through second overhead stream 216. Preferably, second overhead stream 216 comprises more than 50 molar percent, more preferably more than 90 molar percent, and most preferably more than 98 molar percent of the DME that was present in the first overhead stream 210. Second overhead stream 216 also preferably comprises more than 50 molar percent, more preferably more than 90 molar percent, and most preferably more than 98 molar percent of the C4 olefins that were present in the first overhead stream 210. Second bottoms stream 214 preferably comprises a majority of the C5+ hydrocarbons that were present in the first overhead stream 210. Preferably, second bottoms stream 214 comprises more than 50 molar percent, more preferably more than 75 molar percent, and most preferably more than 95 molar percent of the C5+ hydrocarbons that were present in the first overhead stream 210.

Second overhead stream 216 is then directed to a DME removal unit, preferably second wash unit 218. In the second wash unit, the second overhead stream 216 contacts a DME removal medium under conditions effective to remove DME therefrom. DME removal medium, e.g., water, is shown entering second wash unit 218 via line 220. The DME removal medium contacts the DME and exits the second wash unit 218 through third bottoms stream 222. Third bottoms stream 222 preferably comprises a majority of the DME that was present in the second overhead stream 216. Preferably, third bottoms stream 222 comprises more than 50 molar percent, more preferably more than 90 molar percent, and most preferably more than 98 molar percent of the DME that was present in the second overhead stream 216. The DME is easily recoverable from the third bottoms stream 222, for example, by distillation, and then optionally recycled to the MTO reactor. The majority of the C4 olefins from second overhead stream 216 exits second wash unit 218 through third overhead stream 224. Preferably, third overhead stream 224 comprises more than 90 molar percent, more preferably more than 95 molar percent, and most preferably more than 99 molar percent of the C4 olefins that were present in the second overhead stream 216. The third overhead stream 224 may contain a minor amount of DME. The DME content in the third overhead stream 224 will depend upon the DME removal medium treating rate, the number of stages and the temperature of the extraction column, and optionally is adjusted to meet the C4 quality requirements as needed.

As discussed above, the present invention is particularly suited for use with an effluent from an MTO reaction system, which is discussed in more detail hereinafter.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene. A non-limiting list of preferable SAPO molecular sieve catalysts includes SAPO-17, SAPO-18, SAPO-34, SAPO-35, SAPO-44, the substituted forms thereof, and mixtures thereof.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkylamines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, DME, diethyl ether or a combination thereof, more preferably methanol and DME, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefins, preferably and predominantly, ethylene and/or propylene, often referred to as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 hr-1, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

As indicated above, an MTO reaction system produces a major amount of ethylene and propylene in addition to C4 olefins. The ethylene and propylene preferably are removed before the initial effluent stream containing C4 olefins and DME is processed according to the present invention. One non-limiting system for separating ethylene and propylene from C4 olefins and DME is discussed in more detail below.

Figure 4:
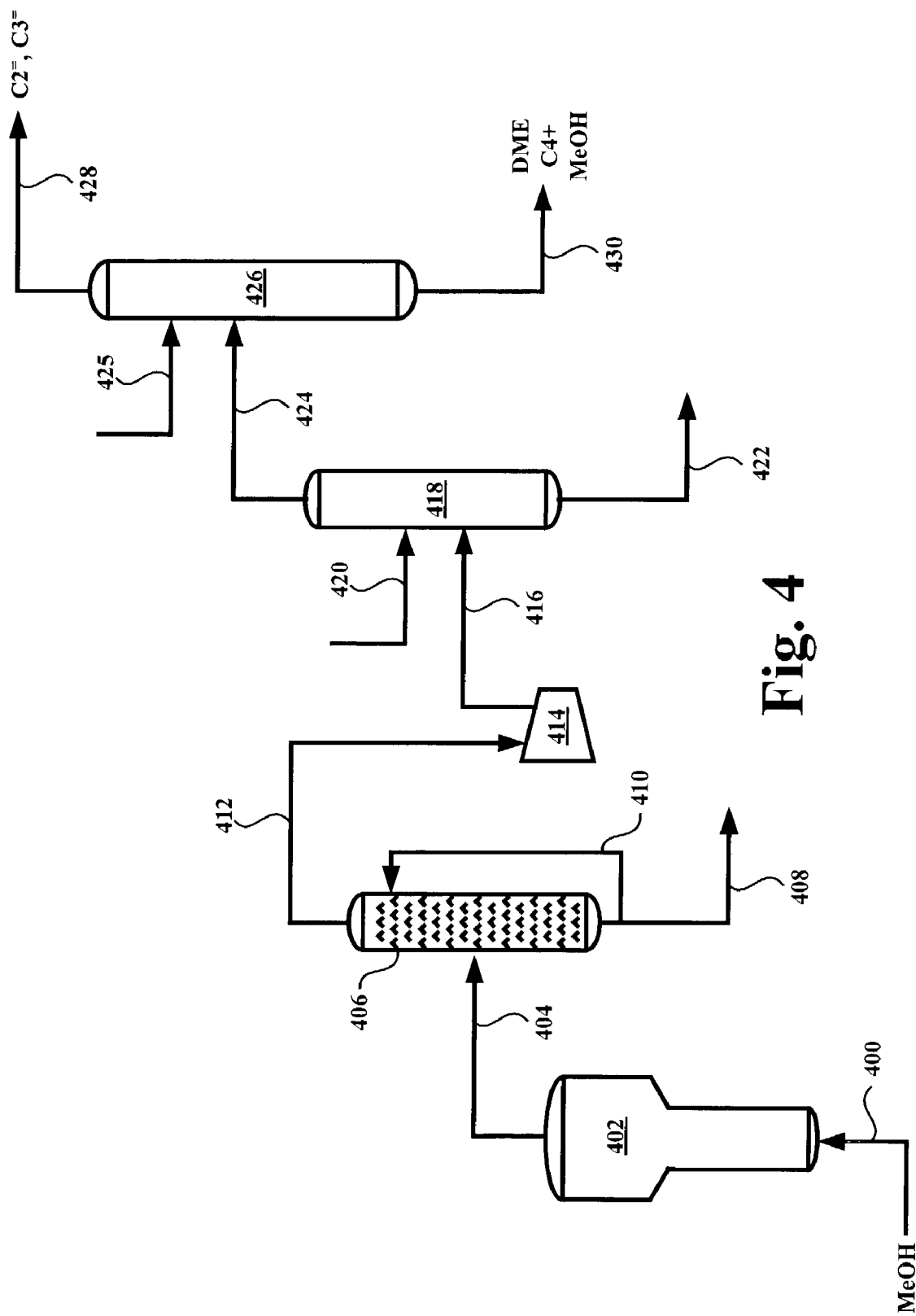
FIG. 4 illustrates an exemplary separation scheme for providing an effluent stream comprising DME, C4 olefins and C5+ hydrocarbons from a product effluent stream of an MTO reaction system.

One example of separating light olefins from C4 olefins and DME is shown in the light olefin removal system of FIG. 4. This example demonstrates one way of obtaining an ethylene and propylene stream substantially depleted of DME and $C_4+$ components. The common factor in this light olefin removal system, however, is that the DME and $C_4+$ components are substantially removed from the ethylene and/or propylene containing stream, e.g., the light olefins stream, prior to caustic treatment of the light olefins stream. This means that both ethylene and propylene are recoverable in a first fraction, with the DME and $C_4+$ components being recoverable in a second fraction. Propane that is present in the olefin stream is recoverable in either the first or second stream, depending upon how low a concentration of DME in the first fraction is desired. The ethylene and propylene optionally are both recovered and further treated, e.g., caustic wash treated or water wash treated, together or separated and treated separately.

FIG. 4 shows one embodiment of the present invention in which the oxygenates and olefins (light and C4+) to be treated are made in an oxygenate to olefin reaction system, more specifically, an MTO reaction system. In FIG. 4, methanol is sent through line 400 to an MTO reactor 402 where the methanol is converted to an olefin-containing stream comprising methane, ethylene, ethane, propylene, propane, DME, $C_4$ olefins, C5+ hydrocarbons, water and other hydrocarbon components. The olefin-containing stream is sent through a line 404 to a quench tower 406 where the olefin is cooled and water and other condensable components are condensed.

The condensed components, which comprise a substantial amount of water, are withdrawn from the quench tower 406 through a bottoms line 408. A portion of the condensed components are circulated through a line 410 back to the top of the quench tower 406. The line 410 contains a cooling unit, e.g., heat exchanger, not shown, to further cool the condensed components so as to provide a cooling medium to further cool the components in quench tower 406.

Olefin vapor leaves through the overhead portion of quench tower 406 through line 412. The olefin vapor is compressed in one or more compressors 414. The compressed olefin optionally passes through line 416 to a water absorption unit 418, where methanol, shown entering the water absorption unit 418 via line 420, is preferably used as the water absorbent. Olefins are recovered through overhead line 424. Optionally, the olefins are sent to one or more additional compressors, not shown, and then are input to a distillation column 426.

The distillation column 426 separates ethylene and propylene, as well as lighter components from the DME and heavier components, including $C_4$ olefins, C5+ hydrocarbons, unreacted methanol, and methanol remaining from the methanol wash. Additional methanol optionally is added to the distillation column 426 though line 425 to reduce hydrate and/or free water formation in the distillation column. The ethylene and propylene containing stream exits the distillation column 426 through overhead line 428, and the heavier components, which include the DME, $C_4$+olefins and C5+ hydrocarbons exit the distillation column 426 through bottoms line 430. Line 428 optionally is directed to a caustic wash unit, a water wash column, and/or a drying unit.

Bottoms line 430 preferably comprises C4 olefins, DME, C5+ hydrocarbons and, optionally, methanol, and is directed to a separation system in accordance with the present invention. That is, in one embodiment, the bottoms line 430 is the "initial effluent stream," referred to above, which is directed to a separation system similar to either of the systems illustrated in FIGS. 1 and 2.

The present invention will be better understood in view of the following non-limiting examples.

EXAMPLE 1

In Example 1, a C4 olefin rich stream was fed to a separation system similar to the separation scheme illustrated in FIG. 1. An initial C4 olefin rich stream, which included water, methanol, propylene, 1-butene, 2-butene (cis and trans), butanes, 1-pentene, pentanes, ethanal, acetone, DME, butadiene, isobutylene, hexene, heptane and other minor components, was directed to a distillation column to provide a first overhead stream comprising C4 olefins and DME and a first bottoms stream comprising methanol and C5+ hydrocarbons. The first overhead stream was directed to a first water wash unit wherein DME was removed from the first overhead stream. The first bottoms stream was directed to a second water wash unit to separate methanol from the second bottoms stream. The first and second water wash units were counter-current liquid/liquid extraction columns. The total water usage to achieve 32 mol ppm DME in the final C4 product for this example was 518 lb.-mol per hour (235 kg-mol per hour), based on a C4 rich stream rate of 100 lb-mol/hr (45 kg-mol/hr). The compositions of the various streams are provided in Table 1, below, with reference to the identification numbers provided in FIG. 1.

TABLE 1

Molar Component Percentages of Processing Streams for Example 1

|  | 102 | 106 | 108 | 114 | 116 | 120 | 122 |
|---|---|---|---|---|---|---|---|
| Water | 7.0 | 0.0 | 11.1 | 98.4 | 0.1 | 26.6 | 0.4 |
| Methanol | 21.7 | 50.1 | 4.9 | 0.6 | 0.0 | 58.4 | 0.0 |
| Propylene | 3.1 | 0.0 | 4.9 | 0.0 | 6.4 | 0.0 | 0.0 |
| 1-butene | 12.0 | 0.3 | 19.1 | 0.0 | 25.2 | 0.0 | 0.0 |
| trans-2-butene | 14.5 | 0.0 | 22.8 | 0.0 | 30.2 | 0.0 | 0.6 |
| cis-2-butene | 14.5 | 0.6 | 22.6 | 0.0 | 29.9 | 0.1 | 1.4 |
| Butanes | 0.4 | 0.0 | 0.7 | 0.0 | 0.9 | 0.0 | 0.0 |
| 1-pentene | 9.6 | 25.9 | 0.0 | 0.0 | 0.0 | 3.4 | 61.7 |
| Pentanes | 0.6 | 1.7 | 0.0 | 0.0 | 0.0 | 0.1 | 4.3 |
| Ethanal | 2.2 | 5.2 | 0.4 | 0.0 | 0.0 | 5.5 | 1.4 |
| Acetone | 1.6 | 4.4 | 0.0 | 0.0 | 0.0 | 3.7 | 3.3 |
| DME | 5.0 | 0.0 | 8.0 | 1.0 | 0.0032 | 0.0 | 0.0 |
| Butadiene | 1.2 | 0.0 | 1.9 | 0.0 | 2.5 | 0.0 | 0.0 |
| Isobutylene | 2.2 | 0.0 | 3.6 | 0.0 | 4.7 | 0.0 | 0.0 |
| Hexenes | 2.3 | 6.1 | 0.0 | 0.0 | 0.0 | 0.8 | 14.6 |
| Hexanes | 0.8 | 2.1 | 0.0 | 0.0 | 0.0 | 0.5 | 4.6 |
| Heptanes | 1.3 | 3.6 | 0.0 | 0.0 | 0.0 | 0.9 | 7.7 |

EXAMPLE 2

In Example 2, a C4 olefin rich stream was fed to separation system similar to the separation scheme illustrated in FIG. 2. An initial C4 olefin rich stream, which included water, methanol, propylene, 1-butene, 2-butene (cis and trans), butanes, 1-pentene, pentanes, ethanal, acetone, DME, butadiene, isobutylene, hexene, heptanes and other minor components, was directed to a first water wash unit, wherein water contacted the initial C4 olefin rich stream to provide a first bottoms stream comprising the water and a majority of the non-DME oxygenates, e.g., methanol, and a first overhead stream comprising C4 olefins, DME and C5+ hydrocarbons. The first overhead stream was directed to a distillation column to provide a second overhead stream comprising C4 olefins and DME and a second bottoms stream comprising the C5+ hydrocarbons. The conditions in the distillation column were adjusted to achieve 95+percent C4 recovery in the second overhead stream, which also contained most of the DME. The second bottoms stream contained almost no oxygenated compounds, so no further treatment of this stream was required. The second overhead stream was then directed to a second water wash unit, wherein water contacted the second overhead stream to provide a third overhead stream comprising the C4 olefins and a third bottoms stream comprising the water and the DME. The first and second water wash units were counter-current liquid/liquid extraction columns. The total water usage to achieve 170 mol ppm DME in the final C4 product for this example was 518 lb.-mol per hour (235 kg-mol per hour), based on a C4 rich stream rate of 100 lb.-mol/hr (45 kg-mol/hr). The compositions of the various streams are provided in Table 2, below, with reference to the identification numbers provided in FIG. 2.

TABLE 2

Molar Component Percentages of Processing Streams for Example 2

|  | 202 | 208 | 210 | 214 | 216 | 224 | 222 |
|---|---|---|---|---|---|---|---|
| Water | 7.0 | 38.0 | 0.4 | 0.0 | 0.5 | 0.1 | 99.0 |
| Methanol | 21.7 | 53.6 | 0.2 | 0.0 | 0.3 | 0.0 | 0.0 |
| Propylene | 3.1 | 0.0 | 4.4 | 0.0 | 5.7 | 6.2 | 0.0 |
| 1-butene | 12.0 | 0.3 | 17.4 | 0.0 | 22.5 | 24.8 | 0.0 |
| trans-2-butene | 21.5 | 0.4 | 20.9 | 0.0 | 27.1 | 29.9 | 0.0 |
| cis-2-butene | 14.5 | 0.4 | 20.9 | 0.0 | 27.1 | 29.9 | 0.0 |
| Butanes | 0.4 | 0.0 | 0.6 | 0.0 | 0.8 | 0.9 | 0.0 |
| 1-pentene | 9.6 | 0.2 | 13.9 | 61.2 | 0.1 | 0.1 | 0.0 |
| Pentanes | 0.6 | 0.0 | 0.9 | 4.0 | 0.0 | 0.0 | 0.0 |
| Ethanal | 2.2 | 3.5 | 1.1 | 0.0 | 1.5 | 0.0 | 0.2 |
| Acetone | 1.6 | 1.4 | 1.6 | 6.9 | 0.0 | 0.0 | 0.0 |
| DME | 5.0 | 1.9 | 6.2 | 0.0 | 8.1 | 0.017 | 0.8 |
| Butadiene | 1.2 | 0.0 | 1.7 | 0.0 | 2.3 | 2.5 | 0.0 |
| Isobutylene | 2.2 | 0.0 | 3.2 | 0.0 | 4.2 | 4.6 | 0.0 |
| Hexenes | 2.3 | 0.1 | 3.3 | 14.5 | 0.0 | 0.0 | 0.0 |
| Hexanes | 0.8 | 0.0 | 1.1 | 4.9 | 0.0 | 0.0 | 0.0 |
| Heptanes | 1.3 | 0.1 | 1.9 | 8.4 | 0.0 | 0.0 | 0.0 |

EXAMPLE 3 (COMPARATIVE)

Figure 3:
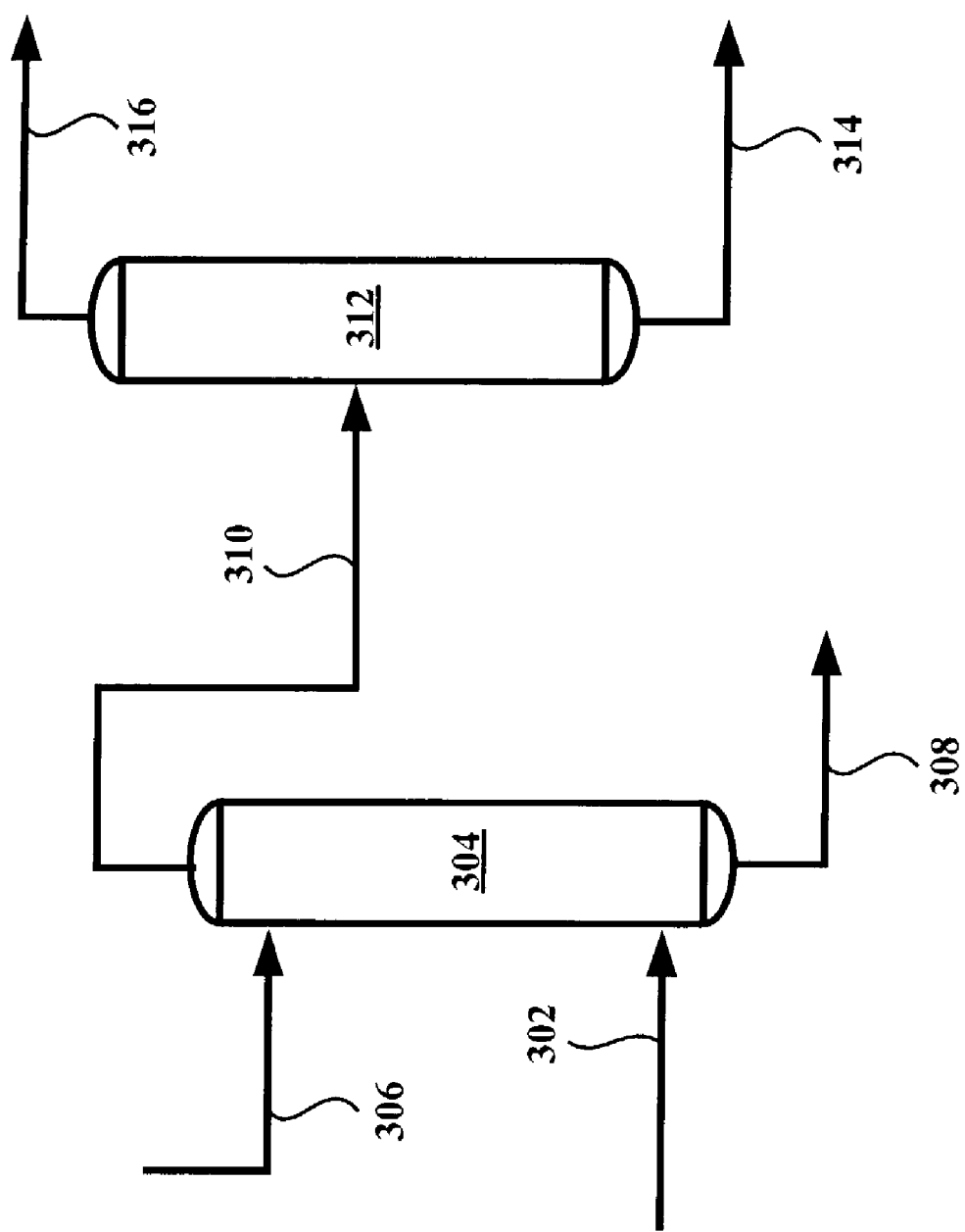
FIG. 3 illustrates a comparison separation scheme.

The separation system of Example 3 is illustrated in FIG. 3, which is discussed in more detail herein. In FIG. 3, effluent stream 302, comprising C5+ hydrocarbons, C4 olefins, and DME, is shown entering wash unit 304. In the wash unit, an oxygenate removal medium, such as water, contacts the effluent stream 302 under conditions effective to separate the oxygenates, e.g., methanol and DME, from the C4 olefins and C5+ hydrocarbons. The oxygenate removal medium is shown entering the wash unit 304 via line 306. Specifically, wash unit 304 separates effluent stream 302 into a first bottoms stream 308 comprising oxygenates such as methanol and DME, and a first overhead stream 310 comprising C4 olefins and C5+ hydrocarbons. The first overhead stream 310 is then directed to a distillation column 312, wherein the first overhead stream 310 is subjected to conditions effective to separate more volatile components from less volatile components contained therein. A second overhead stream 316 comprising more volatile components, e.g., the C4 olefins from first overhead stream 310, exits an upper section of the distillation column 312 and less volatile components, e.g., the C5+ hydrocarbons from first overhead stream 310, exit the distillation column 312 through second bottoms stream 314.

Example 3 is a comparative example wherein a C4 olefin rich stream was fed to a separation system comprising a single wash unit, e.g., extraction column, to remove DME and oxygenates that coboil with C5+ hydrocarbons, e.g., methanol, in a single step, as shown in FIG. 3. The hydrocarbon overhead stream from the extraction column was then fed to a C4/C5+distillation column, wherein conditions were adjusted to achieve 95 percent recovery of C4 olefins in the overhead product. The wash unit was a liquid-liquid extraction column. A large flow of water (543 lb.-mol (246 kg-mol) water per 100 lb.-mol (45 kg-mol) hydrocarbon) was required in the wash unit in order to attempt to remove the DME from the hydrocarbons (unlike Example 2, where a small rate of water was used so that most of the DME remained in the hydrocarbon stream). When a large flow of water was used in a single wash unit, as in Example 3, the DME content in the C4 olefin stream was 1.778 ppm. The separation scheme of Example 3 failed to satisfactorily separate the DME from the C4 olefins, as indicated by the molar component percentages of the various streams provided in Table 3, below.

TABLE 3

Molar Component Percentages of Processing Streams for Example 3

|  | 302 | 308 | 310 | 314 | 316 |
|---|---|---|---|---|---|
| Water | 7.0 | 94.7 | 0.1 | 0.0 | 0.1 |
| Methanol | 21.7 | 3.7 | 0.0 | 0.0 | 0.0 |
| Propylene | 3.1 | 0.0 | 4.8 | 0.0 | 6.3 |
| 1-butene | 12.0 | 0.0 | 19.2 | 0.0 | 25.0 |
| trans-2-butene | 12.5 | 0.0 | 23.1 | 0.0 | 30.1 |
| cis-2-butene | 14.5 | 0.0 | 23.1 | 0.0 | 30.1 |
| Butanes | 0.4 | 0.0 | 0.7 | 0.0 | 0.9 |
| 1-pentene | 9.6 | 0.0 | 15.4 | 65.6 | 0.1 |
| Pentanes | 0.6 | 0.0 | 1.0 | 4.3 | 0.0 |
| Ethanal | 2.2 | 0.4 | 0.0 | 0.0 | 0.0 |
| Acetone | 1.6 | 0.3 | 0.0 | 0.0 | 0.0 |
| DME | 5.0 | 0.8 | 0.1 | 0.0 | 0.1778 |
| Butadiene | 1.2 | 0.0 | 1.9 | 0.0 | 2.5 |
| Isobutylene | 2.2 | 0.0 | 3.6 | 0.0 | 4.7 |
| Hexenes | 2.3 | 0.0 | 3.6 | 15.6 | 0.0 |
| Hexanes | 0.8 | 0.0 | 1.2 | 5.4 | 0.0 |
| Heptanes | 1.3 | 0.0 | 2.1 | 9.2 | 0.0 |

Table 4, below, summarizes the results of Examples 1 to 3 for 100 lb.-mol/hr of a typical C4 rich stream. The inventors observed that, with similar water usage and cooling/heating duties, the DME in the final C4 olefins stream of Example 1 was surprisingly and unexpectedly 56 times less than the DME in the final C4 olefins stream of Example 3, and the DME in final C4 olefins stream of Example 2 was surprisingly and unexpectedly 10 times less than the DME in the final C4 olefins stream of Example 3. The process schemes of Examples 1 and 2 showed a significant advantage in removing DME from C4 olefins compared with Example 3, since a much cleaner C4 product was obtained at lower water usage rates.

TABLE 4

Summary of Simulation Results for 100 lb.-mol/hr (45 kg-mol/hr) of a Typical C4 Rich Stream.

|  | Ex. 1 | Ex. 2 | Ex. 3 |
|---|---|---|---|
| Water Usage, C4 Extraction (lb.-mol/hr) [(kg-mol/hr)] | 509 [231] | 509 [231] | N/A |
| Water Usage, C5 Extraction (lb.-mol/hr) [(kg-mol/hr)] | 9 [4] | N/A | N/A |
| Water Usage, Combined Extraction (lb.-mol/hr) [(kg-mol/hr)] | N/A | 9 [4] | 543 [246] |
| Total Water Usage (lb.-mol/hr) [kg-mol/hr)] | 518 [235] | 518 [235] | 543 [246] |
| Condenser/Reboiler Duty (MBtu/hr) [(MJ/hr)] | −1.50/ 1.53 [−1.58/ 1.61] | −1.77/ 1.83 [−1.87/ 1.93] | −1.63/ 1.83 [−1.72/ 1.93] |
| C4 Olefins Concentration (mole fraction) | 0.9262 | 0.9178 | 0.9241 |
| C4 Olefins Recovery (mole fraction) | 0.9900 | 0.9876 | 0.9970 |
| Overall C4 Recovery (mole fraction) | 0.9902 | 0.9877 | 0.9971 |
| DME in Final C4 Olefins Stream (ppm) | 32 | 170 | 1778 |
| MeOH in First Aq. Stream (mole fraction) | 0.5845 | 0.5361 | 0.0373 |
| DME in First Aq. Stream (mole fraction) | 0.0000 | 0.0185 | 0.00849 |
| Water in First Aq. Stream (mole fraction) | 0.2657 | 0.3796 | 0.9473 |
| DME in Second Aq. Stream (mole fraction) | 0.00955 | 0.00828 | N/A |
| Water in Second Aq. Stream (mole fraction) | 0.9837 | 0.9895 | N/A |

Having now fully described the invention, it will be appreciated by those skilled in the art that the invention may be performed within a wide range of parameters within what is claimed, without departing from the spirit and scope of the invention.

We claim:

1. A process for removing DME from a first stream containing C4 olefins, the process comprising the steps of:
   (a) separating a product effluent from a methanol-to-olefin reactor system into a light olefin stream comprising ethylene and propylene, and the first stream, wherein the first steam comprises C4 olefins, C5+ hydrocarbons, DME, and methanol;
   (b) separating the first stream into a second stream comprising the C4 olefins and the DME, and a third stream comprising the C5+ hydrocarbons and the methanol; and
   (c) contacting the second stream with water in a DME absorption unit under conditions effective to separate the C4 olefins from the DME.

2. The process of claim 1, wherein the separating comprises distilling the first stream under conditions effective to form the second and third streams.

3. The process of claim 2, wherein the process further comprises the step of:
   (d) contacting the third stream with water in a methanol absorption unit under conditions effective to separate the C5+ hydrocarbons from the methanol.

4. The process of claim 1, wherein die process further comprises the step of:
   (d) contacting methanol in a feedstock with a catalyst in the methanol-to-olefin reactor system under conditions effective to convert the methanol in the feedstock to the ethylene and the propylene.

5. The process of claim 4, wherein the catalyst is a silicoaluminophosphate catalyst.

6. The process of claim 5, wherein the catalyst is selected from the group consisting of SAPO-17, SAPO-18, SAPO-34, SAPO-35, SAPO-44, the substituted forms thereof, and mixtures thereof.

7. The process of claim 1, wherein the first stream is derived from a product effluent of a reaction selected from the group consisting of an olefin interconversion reaction, an oxygenate to gasoline conversion reaction, malaeic anhydride formulation, vapor phase methanol synthesis, phthalic anhydride formulation, a Fischer Tropsch reaction, and an acrylonitrile formulation.

8. A process for removing DME from an initial stream including C4 olefins, the process comprising the steps of:
   (a) separating a product effluent from a methanol-to-olefin reactor system into a light olefin stream comprising ethylene and propylene, and the initial stream, wherein the initial stream comprises C4 olefins, C5+ hydrocarbons, DME, and methanol;

(b) contacting the initial stream with water in a methanol removal unit under conditions effective to separate the stream into a first overhead stream comprising the C4 olefins, the DME and the C5+ hydrocarbons, and a first bottoms stream comprising the methanol;

(c) separating the first overhead stream into a second overhead stream comprising the C4 olefins and the DME, and a second bottoms stream comprising the C5+ hydrocarbons; and (d) contacting the second overhead stream with water in a DME removal unit under conditions effective to separate the second overhead stream into a third overhead stream comprising the C4 olefins and a third bottoms stream comprising the DME.

9. The process of claim 8, wherein the separating comprises distilling the first overhead stream under conditions effective to form the second overhead stream and the second bottoms stream.

10. The process of claim 8, wherein the process further comprises the step of:

(e) contacting methanol in a feedstock with a catalyst in the methanol-to-olefin reactor system under conditions effective to convert the methanol in the feedstock to the ethylene and the propylene.

11. The process of claim 10, wherein the catalyst is a silicoaluminophosphate catalyst.

12. The process of claim 11, wherein the catalyst is selected from the group consisting of SAPO-17, SAPO-18, SAPO-34, SAPO-35, SAPO-44, the substituted forms thereof, and mixtures thereof.

13. The process of claim 8, wherein the initial stream is derived from a product effluent of a reaction selected from the group consisting of an olefin interconversion reaction, an oxygenate to gasoline conversion reaction, malaeic anhydride formulation, vapor phase methanol synthesis, phthalic anhydride formulation, a Fischer Tropsch reaction, and an acrylonitrile formulation.

14. A process for removing DME from a product stream of a methanol-to-olefin reaction system, the process comprising the steps of:

(a) separating a product effluent from the methanol-to-olefin reaction system into a light olefin stream comprising ethylene and propylene, and the product stream, wherein the product stream comprises C4 olefins, DME, less than 25 molar percent C5+ hydrocarbons, and less than 35 molar percent methanol; and (b) contacting the product stream with water in a DME removal unit under conditions effective to form an overhead steam comprising the C4 olefins and a bottoms stream comprising the DME.

15. The process of claim 14, wherein the product stream comprises less than 20 molar percent C3-hydrocarbons.

16. The process of claim 15, wherein the product stream comprises less than 10 molar percent C3-hydrocarbons.

17. The process of claim 16, wherein the product stream comprises less than 2 molar percent C3-hydrocarbons.

18. The process of claim 14, wherein the product stream comprises less than 15 molar percent C5+ hydrocarbons.

19. The process of claim 15, wherein the product stream comprises less than 10 molar percent C5+ hydrocarbons.

20. The process of claim 14, wherein the product stream comprises less than 20 molar percent methanol.

21. The process of claim 20, wherein the product stream comprises less than 2 molar percent methanol.

22. The process of claim 14, wherein the process further comprises the step of:

(c) contacting methanol in a feedstock with a catalyst in the methanol-to-olefin reaction system under conditions effective to convert the methanol in the feedstock to the ethylene and the propylene.

23. The process of claim 22, wherein the catalyst is a silicoaluminophosphate catalyst.

24. The process of claim 23, wherein the catalyst is selected from the group consisting of SAPO-17, SAPO-18, SAPO-34, SAPO-35, SAPO-44, the substituted forms thereof, and mixtures thereof.

25. A process for removing DME from a product stream from an methanol-to-olefin reaction system, the process comprising the steps of:

(a) separating a product effluent from the methanol-to-olefin reaction system into a light olefin stream comprising ethylene and propylene, and the product stream, wherein the product stream comprises greater than 30 combined molar percent of DME and C4 olefins; and (b) contacting the stream with water in a DME removal unit under conditions effective to separate the C4 olefins from the DME.

26. The process of claim 25, wherein the ratio of 1-butene to the sum of isobutene, butadiene and 2-butene is greater than 0.1.

27. The process of claim 26, wherein the ratio of 1-butene to the sum of isobutene, butadiene and 2-butene is greater than 0.2.

28. The process of claim 27, wherein die ratio of 1-butene to the sum of isobutene, butadiene and 2-butene is greater than 0.25.

29. The process of claim 25, wherein the product stream comprises greater than 40 combined molar percent of DME and C4 olefins.

30. The process of claim 29, wherein the product stream comprises greater than 60 combined molar percent of DME and C4 olefins.

31. The process of claim 25, wherein the process further comprises the step of:

(c) contacting methanol in a feedstock with a catalyst in the methanol-to-olefin reaction system under conditions effective to convert the methanol in the feedstock to the ethylene and the propylene.

32. The process of claim 31, wherein the catalyst is a silicoaluminophosphate catalyst.

33. The process of claim 32, wherein the catalyst is selected from the group consisting of SAPO-17, SAPO-18, SAPO-34, SAPO-35, SAPO-44, the substituted forms thereof, and mixtures thereof.

34. A process for removing DME from a product stream from a methanol-to-olefin reaction system, the process comprising the steps of:

(a) separating a product effluent from the methanol-to-olefin reaction system into a light olefin stream comprising ethylene and propylene, and the product stream, wherein the product stream comprises DME, butenes, C5+ hydrocarbons and coboiling oxygenates;

(b) removing the C5+ hydrocarbons and the coboiling oxygenates from the product stream to form a processed stream comprising the DME and the butenes; and (c) contacting the processed stream with water in a DME removal unit under conditions effected to separate the DME from the butenes.

35. The process of claim 34, wherein the process further comprises the step of:

(d) contacting methanol in a feedstock with a catalyst in the methanol-to-olefin reaction system under conditions effective to convert the methanol in the feedstock to the ethylene and the propylene.

36. The process of claim 35, wherein the catalyst is a silicoaluminophosphate catalyst.

37. The process of claim 36, wherein the catalyst is selected from the group consisting of SAPO-17, SAPO-18, SAPO-34, SAPO-35, SAPO-44, the substituted forms thereof, and mixtures thereof.

38. The process of claim 34, wherein the processed stream comprises greater than 0.5 molar percent DME.

39. The process of claim 38, wherein the processed stream comprises greater than 2 molar percent DME.

40. The process of claim 39, wherein the processed stream comprises greater than 10 molar percent DME.

* * * * *